(12) United States Patent
Gualberto

(10) Patent No.: US 12,734,161 B2
(45) Date of Patent: Sep. 15, 2026

(54) METHOD OF TREATING BREAST CANCER

(71) Applicant: Eisai R&D Management Co., Ltd., Tokyo (JP)

(72) Inventor: Antonio Gualberto, Boston, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 553 days.

(21) Appl. No.: 18/035,091

(22) PCT Filed: Nov. 5, 2021

(86) PCT No.: PCT/US2021/058185
§ 371 (c)(1),
(2) Date: May 2, 2023

(87) PCT Pub. No.: WO2022/098953
PCT Pub. Date: May 12, 2022

(65) Prior Publication Data

US 2023/0404987 A1 Dec. 21, 2023

Related U.S. Application Data

(60) Provisional application No. 63/195,505, filed on Jun. 1, 2021, provisional application No. 63/117,678, filed on Nov. 24, 2020, provisional application No. 63/110,800, filed on Nov. 6, 2020, provisional application No. 63/110,787, filed on Nov. 6, 2020.

(51) Int. Cl.
*A61K 31/4439* (2006.01)
*A61P 35/00* (2006.01)

(52) U.S. Cl.
CPC .......... *A61K 31/4439* (2013.01); *A61P 35/00* (2018.01)

(58) Field of Classification Search
None
See application file for complete search history.

(56) References Cited

U.S. PATENT DOCUMENTS

2016/0347717 A1* 12/2016 Brock et al.

FOREIGN PATENT DOCUMENTS

| | | |
|---|---|---|
| WO | WO 2018/097273 A1 | 5/2018 |
| WO | WO 2018/170447 A1 | 9/2018 |
| WO | WO 2020/132437 A1 | 6/2020 |
| WO | WO 2020/242795 A1 | 12/2020 |

OTHER PUBLICATIONS

Chandrarlapaty et al. (JAMA Oncol. 2016:2(10):1310-1315) (Year: 2016).*
Guo et al. (Breast Cancer Res Treat. 2020; 180(2): 359-368). (Year: 2020).*
Santo et al. (Cancers 2019; 11: 1894) (Year: 2019).*
(Continued)

*Primary Examiner* — Brandon J Fetterolf
(74) *Attorney, Agent, or Firm* — Finnegan, Henderson, Farabow, Garrett & Dunner, LLP

(57) ABSTRACT

The present invention relates to methods of treating breast cancer patients with Compound 1 or pharmaceutically acceptable salts thereof. In some embodiments, the invention relates to treating patients meeting mutant allele frequency threshold values.

17 Claims, 5 Drawing Sheets

Specification includes a Sequence Listing.

(56) References Cited

OTHER PUBLICATIONS

Furman et al., (2020) "First-in-Class Oral Selective ER Covalent Antagonist (SERCA) H3B-6545 Demonstrates Encouraging Preclinical and Clinical Activity in ER+/HER2-Breast Cancer", *San Antonio Breast Cancert Symposium*—Dec. 8-11, 2020, Abstract #918.
Hamilton et al., (2019) "Phase 1 Dose Escalation of H3B-6545, a First-in-Class Highly Selective ERα Covalent Antagonist (SERCA), in Women with ER-positive, HER2-negative Breast Cancer" *Clinical Oncology Annual Meeting*—Jun. 2, 2019, Abstract #1059.
Hamilton et al., (2020) "Phase 1 Dose Escalation of H3B-6545, a First-in-Class Highly Selective ERα Covalent Antagonist (SERCA), in Women with ER-positive, HER2-negative Breast Cancer (HR+ BC)", ASCO Meeting Library.
Rimkunas et al., (2019) "Molecular characterization and monitoring of patient ctDNA in phase I study of H3B-6545 in ER+ MBC", *ASCO Meeting Library*, 2 pages.
Rimkunas et al., (2019) "Molecular Characterization and Monitoring of Patient ctDNA in Phase I Study of H3B-6545 in ER+ MBC", *American Society of Clinical Oncology*—Jun. 2, 2019, Abstract #1052.
Furman et al., (2019) "Estrogen Receptor Covalent Antagonists: The Best Is Yet to Come", *Cancer Research*, 79(8):1740-1745.
Hamilton et al., (2021) "Phase I/II study of H3B 6545, a novel selective estrogen receptor covalent antagonist (SERCA), in estrogen receptor positive (ER+), human epidermal growth factor receptor 2 negative (HER2−) advanced breast cancer" URL:https://aacrjournals.org/cancerres/article/81 /4_Supplement/PD8-06/648035/Abstract-PD8-06-Phase-I-II-trial-of-H3B-6545-a; Feb. 15, 2021 (4 pages).
Hamilton et al., (2021) "Phase I/II study of H3B 6545, a novel selective estrogen receptor covalent antagonist (SERCA), in estrogen receptor positive (ER+), human epidermal growth factor receptor 2 negative (HER2−) advanced breast cancer" *J. of Clinical Oncology*, URL:https://ascopubs.org/doi/abs/10.1200/JCO.2021.39.15_suppl.1018; May 28, 2021 (4 pages).
Hamilton et al., (2021) "Phase I/II study of H3B 6545, a novel selective estrogen receptor covalent antagonist (SERCA), in estrogen receptor positive (ER+), human epidermal growth factor receptor 2 negative (HER2−) advanced breast cancer" *American Society of Clinical Oncology Annual Meeting*—Jun. 4-8, 2021, Abstract #337389.
International Patent Application No. PCT/US2021/058185, filed Nov. 5, 2021, by Eisai R&D Management Co., Ltd., International Search Report and Written Opinion, mailed Mar. 1, 2022 (19 pages).
Korpal et al., (2021) "Abstract PS12-23: Development of H38-6545, a first-in-class oral selective ER covalent antagonist (SERCA), for the treatment of ERαWT and ERαMUT breast cancer", *Cancer Research*,81(4_supplement) (4 pages).
Puyang et al., (2018) "Discovery of Selective Estrogen Receptor Covalent Antagonists for the Treatment of $ER\alpha^{WT}$ and $ER\alpha^{MUT}$ Breast Cancer", *Cancer Discovery*, 8(9):1176-1193.
Rimkunas et al., "Molecular characterization and montioring of patient ctDNA in phase I study of H3B-6545 in ER+ MBC", *Journal of Oncology*, 37(15) (4 pages).

* cited by examiner

CLONAL Y537S, N=10, 8 EVENTS, MEDIAN (95% CI) = 7.3(0.8, 11.2) MONTHS
CLONAL D538G, N=19, 13 EVENTS, MEDIAN (95% CI) = 5.4(1.7, 7.2) MONTHS
POLYCLONAL Y537S AND D538G, N=4, 3 EVENTS, MEDIAN (95% CI) = 3.5(1.7, 5.4) MONTHS
Y537S AND D538G NEGATIVES, N=61, 33 EVENTS, MEDIAN (95% CI) = 3.8(2.0, 7.3) MONTHS

SEQUENCE LISTING

<160> NUMBER OF SEQ ID NOS: 2

<210> SEQ ID NO 1
<211> LENGTH: 595
<212> TYPE: PRT

-continued

<213> ORGANISM: Homo sapiens

<400> SEQUENCE: 1

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400
```

-continued

Lys Leu Leu Phe Ala Pro Asn Leu Leu Leu Asp Arg Asn Gln Gly Lys
405 410 415

Cys Val Glu Gly Met Val Glu Ile Phe Asp Met Leu Leu Ala Thr Ser
420 425 430

Ser Arg Phe Arg Met Met Asn Leu Gln Gly Glu Glu Phe Val Cys Leu
435 440 445

Lys Ser Ile Ile Leu Leu Asn Ser Gly Val Tyr Thr Phe Leu Ser Ser
450 455 460

Thr Leu Lys Ser Leu Glu Glu Lys Asp His Ile His Arg Val Leu Asp
465 470 475 480

Lys Ile Thr Asp Thr Leu Ile His Leu Met Ala Lys Ala Gly Leu Thr
485 490 495

Leu Gln Gln Gln His Gln Arg Leu Ala Gln Leu Leu Leu Ile Leu Ser
500 505 510

His Ile Arg His Met Ser Asn Lys Gly Met Glu His Leu Tyr Ser Met
515 520 525

Lys Cys Lys Asn Val Val Pro Leu Tyr Asp Leu Leu Leu Glu Met Leu
530 535 540

Asp Ala His Arg Leu His Ala Pro Thr Ser Arg Gly Gly Ala Ser Val
545 550 555 560

Glu Glu Thr Asp Gln Ser His Leu Ala Thr Ala Gly Ser Thr Ser Ser
565 570 575

His Ser Leu Gln Lys Tyr Tyr Ile Thr Gly Glu Ala Glu Gly Phe Pro
580 585 590

Ala Thr Val
595

<210> SEQ ID NO 2
<211> LENGTH: 2879
<212> TYPE: DNA
<213> ORGANISM: Homo sapiens

<400> SEQUENCE: 2
gtcgcctcta acctcgggct gtgctctttt tccaggtggc ccgccggttt ctgagccttc 60
tgccctgcgg ggacacggtc tgcaccctgc ccgcggccac ggaccatgac catgaccctc 120
cacaccaaag catctgggat ggccctactg catcagatcc aagggaacga gctggagccc 180
ctgaaccgtc cgcagctcaa gatccccctg gagcggcccc tgggcgaggt gtacctggac 240
agcagcaagc ccgccgtgta caactacccc gagggcgccg cctacgagtt caacgccgcg 300
gccgccgcca acgcgcaggt ctacggtcag accggcctcc cctacggccc cgggtctgag 360
gctgcggcgt tcggctccaa cggcctgggg ggtttccccc cactcaacag cgtgtctccg 420
agcccgctga tgctactgca cccgccgccg cagctgtcgc ctttcctgca gccccacggc 480
cagcaggtgc cctactacct ggagaacgag cccagcggct acacggtgcg cgaggccggc 540
ccgccggcat tctacaggcc aaattcagat aatcgacgcc agggtggcag agaaagattg 600
gccagtacca atgacaaggg aagtatggct atggaatctg ccaaggagac tcgctactgt 660
gcagtgtgca atgactatgc ttcaggctac cattatggag tctggtcctg tgagggctgc 720
aaggccttct tcaagagaag tattcaagga cataacgact atatgtgtcc agccaccaac 780
cagtgcacca ttgataaaaa caggaggaag agctgccagg cctgccggct ccgcaaatgc 840
tacgaagtgg gaatgatgaa aggtgggata cgaaaagacc gaagaggagg gagaatgttg 900
aaacacaagc gccagagaga tgatggggag ggcaggggtg aagtggggtc tgctggagac 960

-continued

```
atgagagctg ccaacctttg gccaagcccg ctcatgatca aacgctctaa gaagaacagc   1020

ctggccttgt ccctgacggc cgaccagatg gtcagtgcct tgttggatgc tgagcccccc   1080

atactctatt ccgagtatga tcctaccaga cccttcagtg aagcttcgat gatgggctta   1140

ctgaccaacc tggcagacag ggagctggtt cacatgatca actgggcgaa gagggtgcca   1200

ggctttgtgg atttgaccct ccatgatcag gtccaccttc tagaatgtgc ctggctagag   1260

atcctgatga ttggtctcgt ctggcgctcc atggagcacc cagggaagct actgtttgct   1320

cctaacttgc tcttggacag gaaccaggga aaatgtgtag agggcatggt ggagatcttc   1380

gacatgctgc tggctacatc atctcggttc cgcatgatga atctgcaggg agaggagttt   1440

gtgtgcctca aatctattat tttgcttaat tctggagtgt acacatttct gtccagcacc   1500

ctgaagtctc tggaagagaa ggaccatatc caccgagtcc tggacaagat cacagacact   1560

ttgatccacc tgatggccaa ggcaggcctg accctgcagc agcagcacca gcggctggcc   1620

cagctcctcc tcatcctctc ccacatcagg cacatgagta acaaaggcat ggagcatctg   1680

tacagcatga agtgcaagaa cgtggtgccc ctctatgacc tgctgctgga gatgctggac   1740

gcccaccgcc tacatgcgcc cactagccgt ggaggggcat ccgtggagga gacggaccaa   1800

agccacttgg ccactgcggg ctctacttca tcgcattcct tgcaaaagta ttacatcacg   1860

ggggaggcag agggtttccc tgccacggtc tgagagctcc ctggctccca cacggttcag   1920

ataatccctg ctgcatttta ccctcatcat gcaccacttt agccaaattc tgtctcctgc   1980

atacactccg gcatgcatcc aacaccaatg gctttctaga tgagtggcca ttcatttgct   2040

tgctcagttc ttagtggcac atcttctgtc ttctgttggg aacagccaaa gggattccaa   2100

ggctaaatct ttgtaacagc tctctttccc ccttgctatg ttactaagcg tgaggattcc   2160

cgtagctctt cacagctgaa ctcagtctat gggttggggc tcagataact ctgtgcattt   2220

aagctacttg tagagaccca ggcctggaga gtagacattt tgcctctgat aagcactttt   2280

taaatggctc taagaataag ccacagcaaa gaatttaaag tggctccttt aattggtgac   2340

ttggagaaag ctaggtcaag ggtttattat agcaccctct tgtattccta tggcaatgca   2400

tccttttatg aaagtggtac accttaaagc ttttatatga ctgtagcaga gtatctggtg   2460

attgtcaatt cattcccccct ataggaatac aaggggcaca cagggaaggc agatccccta   2520

gttggcaaga ctattttaac ttgatacact gcagattcag atgtgctgaa agctctgcct   2580

ctggctttcc ggtcatgggt tccagttaat tcatgcctcc catggaccta tggagagcag   2640

caagttgatc ttagttaagt ctccctatat gagggataag ttcctgattt ttgtttttat   2700

ttttgtgtta caaaagaaag ccctccctcc ctgaacttgc agtaaggtca gcttcaggac   2760

ctgttccagt gggcactgta cttggatctt cccggcgtgt gtgtgcctta cacaggggtg   2820

aactgttcac tgtggtgatg catgatgagg gtaaatggta gttgaaagga gcaggggcc    2879
```

METHOD OF TREATING BREAST CANCER

CROSS-REFERENCE TO RELATED APPLICATIONS

This application claims the benefit of priority of US Provisional Application Nos. 63/110,787, filed Nov. 6, 2020; 63/110,800, filed Nov. 6, 2020; 63/117,678, filed Nov. 24, 2020; and 63/195,505, filed Jun. 1, 2021, the contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 4, 2021, is named 15647_0015-00304_SL.txt and is 9,309 bytes in size.

FIELD

Embodiments relate to methods of treating breast cancer patients, and particularly patients having breast cancer tumors expressing the estrogen receptor alpha (ERα) protein.

BACKGROUND

Breast cancer is the most commonly diagnosed malignancy among women today with nearly 200,000 new cases diagnosed in the US and 1.7 million new cases diagnosed worldwide each year. Since about 70% of breast tumors are positive for the estrogen receptor alpha protein (ERα protein, encoded by the ESR1 gene)—a key oncogenic driver in this subset of tumors—several classes of therapies have been developed to antagonize ERα function, including 1) selective estrogen receptor degraders (SERDs) of which fulvestrant is an example, 2) selective estrogen receptor modulators (SERMs) of which tamoxifen is an example and 3) aromatase inhibitors that reduce systemic levels of estrogen.

These therapies have been largely effective in the clinic reducing occurrence and progression of ERα+ breast tumors. However there are on-target liabilities associated with these different classes of compounds. For example, tamoxifen has been shown to activate signaling activity in the endometrium leading to an increase in risk of endometrial cancers in the clinic (Fisher et al., (1994) *J Natl Cancer Inst*. April 6; 86(7):527-37; van Leeuwen et al., (1994) *Lancet* February 19; 343(8895):448-52). In contrast, since fulvestrant is a pure antagonist, it can lead to loss of bone density in post-menopausal women as ERα activity is critical for bone building. In addition to on-target side effects, clinical resistance is also beginning to emerge to these classes of ERα antagonists highlighting the need to develop next-generation compounds.

Several mechanisms of resistance have been identified using in vitro and in vivo models of resistance to various endocrine therapies. These include increased ERα/HER2 “crosstalk” (Shou et al., (2004) *J Natl Cancer Inst*. June 16; 96(12):926-35), aberrant expression of ERα coactivators/corepressors (Osborne et al., (2003) *J Natl Cancer Inst*. March 5; 95(5):353-61) or loss of ERα altogether to allow ER-independent growth (Osborne C K, Schiff R (2011) *Annu Rev Med* 62: 233-47).

In the hopes of identifying clinically relevant mechanisms of resistance, great effort has also recently gone into deeply characterizing the genetics of endocrine-therapy resistant metastases isolated from patients. Several independent labs have recently published on a multitude of genetic lesions observed in the resistant vs the primary tumors (Li et al., (2013) *Cell* Rep. September 26; 4(6):1116-30; Robinson et al., (2013) *Nat Genet*. December; 45(12):1446-51; Toy et al., (2013) *Nat Genet*. 2013 December; 45(12):1439-45). Among these are the highly recurrent mutations in the ligand-binding domain of ESR1 (gene which encodes ERα protein), which were found to be significantly enriched in about 20% of resistant tumors relative to endocrine therapy naïve tumors (Jeselsohn et al., (2014) *Clin Cancer Res*. April 1; 20(7):1757-67; Toy et al., (2013) *Nat Genet*. 2013 December; 45(12):1439-45; Robinson et al., (2013) *Nat Genet*. December; 45(12):1446-51; Merenbakh-Lamin et al., (2013) Cancer Res. December 1; 73(23):6856-64; Yu et al., (2014) *Science* July 11; 345(6193):216-20; Segal and Dowsett (2014), *Clin Cancer Res* April 1; 20(7):1724-6), suggesting the potential for these mutations to functionally drive clinical resistance. In contrast to the enrichment in ESR1 mutations observed in therapy-resistant tumors, mutations in other cancer-related genes failed to show such a robust enrichment, strongly implying the importance of ERα mutations in promoting resistance (Jeselsohn et al., (2014) *Clin Cancer Res*. April 1; 20(7):1757-67).

ER+ breast cancer patients on average are treated with seven independent therapies including chemotherapies and various anti-estrogen therapies such as tamoxifen, fulvestrant and aromatase inhibitors. Recent genomic profiling has revealed that the ERα pathway remains a critical driver of tumor growth in the resistant setting as activating mutations in ERα have emerged. Thus, it is critical that more potent ER-directed therapies be developed that can overcome resistance in the clinical setting. Hence, there is a need for novel compounds that can potently suppress the growth of both wild type (WT) and ER α-mutant positive tumors and methods for better targeting such compounds to patients likely to respond to treatment.

One compound that is reportedly useful for treating ER+ breast cancer patients is (E)-N,N-dimethyl-44(2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide, which is shown below as Compound 1:

(Compound 1)

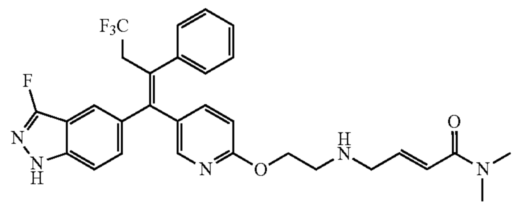

Compound 1 is a selective, orally available, small molecule covalent antagonist of the estrogen receptor (ERα). Compound 1 is reported further in U.S. Pat. No. 9,796,683 B2, “Tetrasubstituted Alkene Compounds and Their Use,” which is incorporated by reference in its entirety as if fully rewritten herein. Compound 1 is reported to bind covalently to a cysteine residue at position 530 of both wild type and the constitutively active mutant ERα proteins, including Y537S. Compound 1 has demonstrated significant antitumor activity in multiple PDX breast cancer models, including those with mutated ESR1 (the gene encoding ERα). Pharmaceutically acceptable salts of that compound have also been reported as useful for treating ER+ breast cancer patients. For example, Compound 1 may be used as a hydrochloride salt, which may be a crystalline form as described in U.S. Pat. No. 10,640,483 B2, which is incorporated by reference in its entirety as if fully rewritten herein. Compound 1 has been formulated as capsules or tablets, as described in Patent Cooperation Treaty Patent Application No. PCT/US2020/033292, filed on May 15, 2020, and incorporated by reference in its entirety as if fully rewritten herein.

BRIEF SUMMARY

Although Compound 1 has been found to be useful for treating ER+ breast cancer patients, it would be useful to better predict which cancer patients would be more responsive to, and therefore more likely to benefit from treatment. One aspect of the present disclosure is directed to use of a patient's mutant allele frequency to better predict the likelihood of favorable response to treatment with Compound 1 or a pharmaceutically acceptable salt thereof.

Various embodiments disclosed herein provide a method of treating a cancer, particularly breast cancer in a patient in need thereof, comprising administering Compound 1 or a pharmaceutically acceptable salt thereof to the patient having a first mutant allele frequency value of a first ESR1 mutant greater than or equal to 0.5%, e.g., in a blood sample, e.g., in a cfDNA in a blood sample. In some embodiments, the patient is further administered one or more cancer treatments, e.g., one or more treatments for breast cancer.

In some embodiments the first ESR1 mutant is at Y537. In some embodiments the first ESR1 mutant is Y537S. In some embodiments the patient has a second mutant allele frequency value of a second ESR1 mutant, and said second mutant allele frequency value is less than 0.5%. In some embodiments the second ESR1 mutant is at D538. In some embodiments the second ESR1 mutant is D538G. In some embodiments the second ESR1 mutant is L536H, L536P, L536Q, L536R, Y537C, Y537N, D538G, or E380Q.

In some embodiments, the first ESR1 mutant is at D538. In some embodiments, the first ESR1 mutant is D538G. In some embodiments the patient has a second mutant allele frequency value of a second ESR1 mutant and said second mutant allele frequency value is less than 0.5%. In some embodiments the second ESR1 mutant is at Y537. In some embodiments the second ESR1 mutant is Y537S. In some embodiments the second ESR1 mutant is L536H, L536P, L536Q, L536R, Y537C, Y537N, Y537S, or E380Q.

In some embodiments the first mutant allele frequency value is greater than 0.6%. In some embodiments the first mutant allele frequency value is greater than 0.7%. In some embodiments the first mutant allele frequency value is greater than 0.8%. In some embodiments the first mutant allele frequency value is greater than 0.9%. In some embodiments the first mutant allele frequency value is greater than 1.0%.

In some embodiments the second mutant allele frequency value is less than 0.4%. In some embodiments the second mutant allele frequency value is less than 0.3%. In some embodiments the second mutant allele frequency value is less than 0.2%. In some embodiments the second mutant allele frequency value is less than 0.1%.

In some embodiments, ERα mutations are measured directly from a tumor sample. In those embodiments, the sample from a patient selected for treatment may indicate the presence of a D537 mutation or the presence of a D538 mutation.

In some embodiments the patient has PgR positive status.

PgR Positive (≥1% positive cells), N=38, 24 events, median (95%)=5.4 (2.0, 8.8) months.

PgR Negative (≤1% positive cells), N=34, 20 events, median (95%)=2.1 (1.7, 7.4) months.

Figure 4:
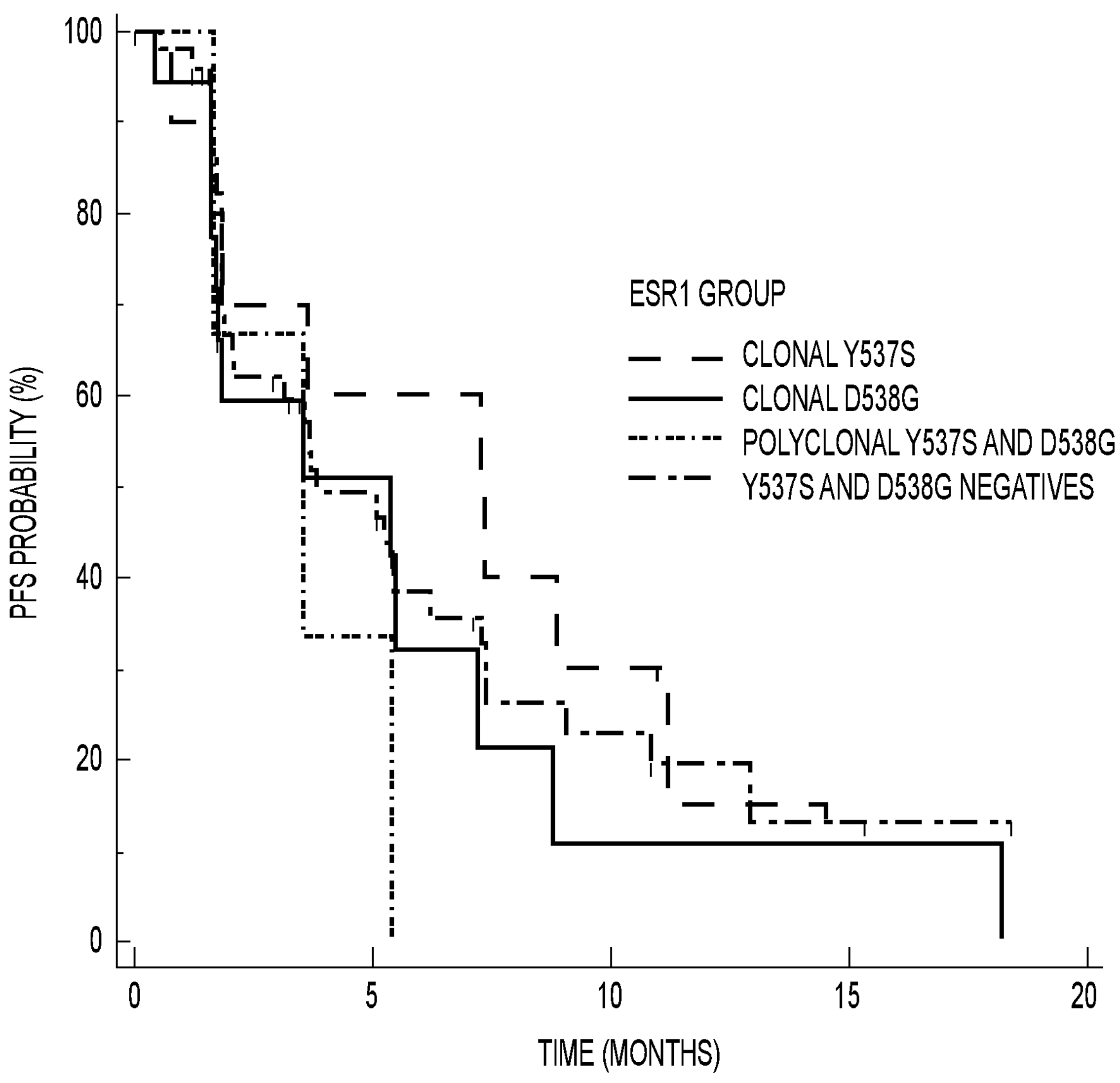

FIG. 4 shows progression free survival according to ESR1 mutation status as reported in Example 3. The text in the inset reads as follows:

Clonal Y537S, N=10, 8 events, median (95% Cl)=7.3 (0.8, 11.2) months.

Clonal D538G, N=19, 13 events, median (95% Cl)=5.4 (1.7, 7.2) months.

Polyclonal Y537S and D538G, N=4, 3 events, median (95% Cl)=3.5 (1.7, 5.4) months.

Y537S and D538G negatives, N=61, 33 events, median (95% Cl)=3.8 (2.0, 7.3) months.

Figure 5:
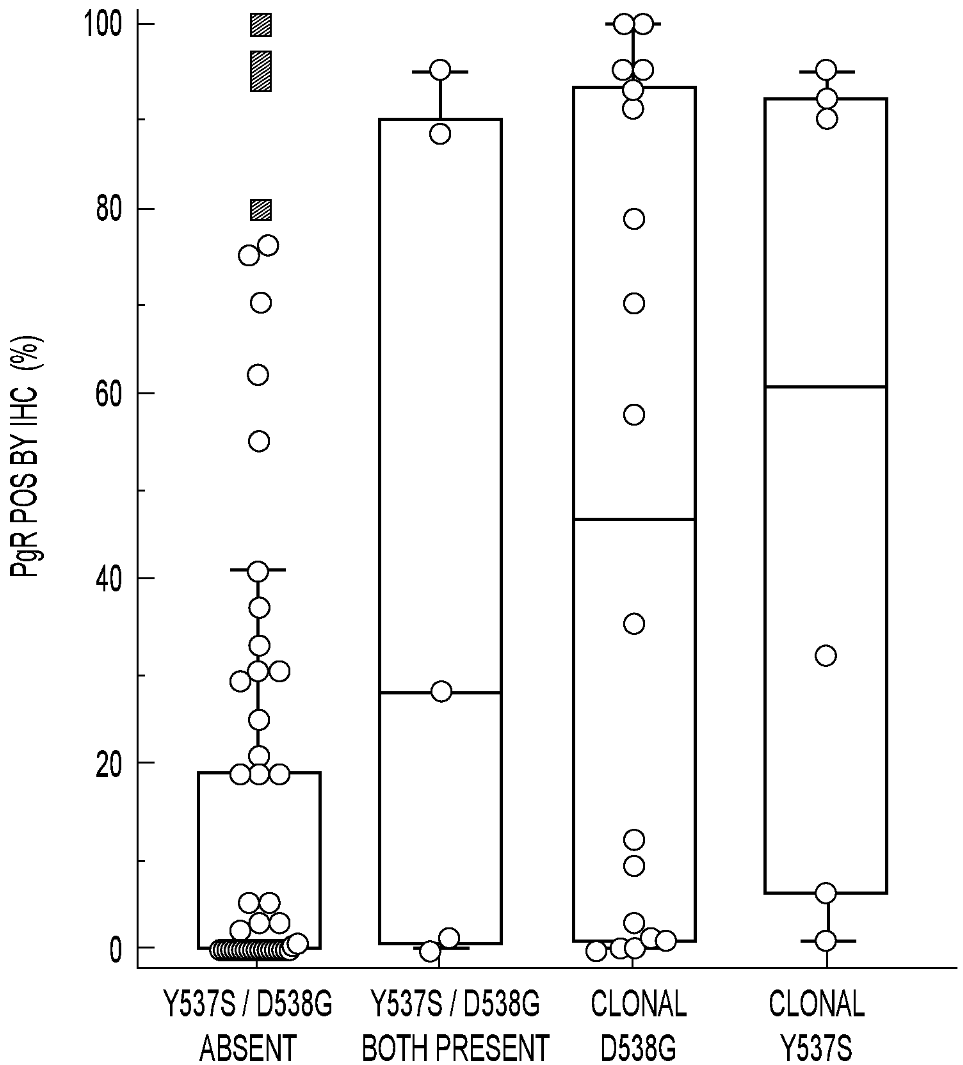

FIG. 5 shows the relationship between the detection of ESR1 mutation in blood and the level of PgR expression in a tumor.

DETAILED DESCRIPTION

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are described herein.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently disclosed subject matter.

The following definitions may be useful for understanding embodiments as presented herein.

As used herein, the term "sample" refers to a material or mixture of materials containing one or more components of interest. A sample from a subject refers to a sample obtained from the subject, including samples of biological tissue or fluid origin, obtained, reached, or collected in vivo or in situ. A sample can be obtained from a region of a subject containing precancerous or cancer cells or tissues or from another tissue or fluid in the subject. Such samples can be, but are not limited to, organs, tissues, fractions and cells isolated from a mammal. Exemplary samples include lymph node, whole blood, partially purified blood, serum, plasma, bone marrow, and peripheral blood mononuclear cells ("PBMC"). A sample also can be a tissue biopsy. Exemplary samples also include cell lysate, a cell culture, a cell line, a tissue, oral tissue, gastrointestinal tissue, an organ, an organelle, a biological fluid, a blood sample, a urine sample, a skin sample, and the like.

As used herein, the term "subject" refers to a mammal. A subject can be a human or a non-human mammal such as a dog, cat, bovid, equine, mouse, rat, rabbit, or transgenic species thereof. In some embodiments, a subject is a human.

cfDNA: As used herein, "cfDNA" refers to cell-free DNA in a subject's blood circulation, and may include DNA from blood cells, viruses, solid organs and many other sources. Xia L. et al. report that over 90% of cfDNA is from debris of blood cells in healthy individuals. (Xia, L. et al., Statistical analysis of mutant allele frequency level of circulating cell-free DNA and blood cells in healthy individuals, Scientific Reports 7:7526; D01:10.1038/s41598-017-06106-1)

As used herein, "ctDNA" refers to circulating tumor DNA in the plasma in cancer patients. Xia L. et al. report that in cancer patients, tumor-related ctDNA comprises 0.1-0.01% of the plasma cfDNA.

As used herein, "wild type" or "WT" refers to the predominant form in which a nucleotide or amino acid sequence exists. The predominant form can be identified in a sample from a subject and/or determined based on the predominant form of the nucleotide or amino acid sequence observed in a subject population, e.g., in the human population. For example, if 80% of nucleotide sequences in the human population contain an adenosine base in a particular location, with the remainder of sequences comprising cytosine, thymine or guanine in that position, wild type is said to have an adenosine in that position. Likewise, if 80% of protein sequences in the human population have a glycine residue in a particular location, with the remainder of sequences comprising some other amino acid residue, glycine is said to be the wild type residue.

A subject or a sample from a subject can have multiple copies of the ESR1 gene. These copies can encode wild type and/or mutant ERα proteins. As used herein, subject or a sample from a subject having an ESR1 mutation can also have one or more copies of the wild type ESR1 gene and/or the wild type ERα protein.

As used herein, "mutant allele frequency" or "MAF" is the ratio expressed as a decimal of the number of individual genetic reads bearing a particular mutation relative to a wild-type sequence at a particular location, divided by the total number of individual genetic reads covering the same locus. For example, for a particular sequence position, if the total sequencing depth is 10,000 with an adenine (A) base accounting for 9,900 distinct occurrences, the remaining distinct sequencing occurrences may include, e.g., 23 occurrences having a thymine (T) base in the same position, 42 occurrences having a cytosine (C) base in the same position, and the remaining 35 occurrences having a guanine (G) base in the same position. As the vast majority of sequences have the adenine base in that position (thereby conferring adenine in that position as the "wild type" base), the mutant allele frequency of having a thymine (T) base is calculated as (T)/(T+C+G+A), or here, $^{23}/_{10000}$=0.0023. Because the skilled artisan understands that the genetic code is redundant, mutant allele frequency can also be calculated based upon codon coding for a particular amino acid in a particular protein sequence. MAF values reflecting amino acid mutations would therefore group all nucleic acid sequences that encode the same mutation. The skilled artisan also appreciates that a single gene may encode amino acid mutations in different locations. Hence, MAF values may be calculated for multiple amino acid mutations at different locations in a single gene.

As used herein, a "mutant ERα protein" is a non-wild type ERα protein that contains at least one amino acid mutation relative to wild type (the protein may also be referred to as mutant "ESR1"). As used herein, an "ESR1 mutant" refers to at least one mutation in an ESR1 gene encoding an ERα protein. An "ERα MAF" or an "ESR1 MAF" refers to the frequency of an ESR1 mutant encoding a mutant ERα protein. In some embodiments, the wild type ESR1 gene is SEQ ID NO: 2. In some embodiments, the amino acid sequence of the wild type ERα protein is SEQ ID NO: 1.

As used herein, a "constitutively active mutant" is a non-wild type protein that is active without the need of a bound ligand, e.g., an ERα protein active even in the absence of estrogen.

Those of skill in the art will recognize that various methods and techniques may be used to assay MAF, including sequencing techniques known in the art, such as next-generation sequencing (NGS) and droplet digital PCR (ddPCR). For example, one useful tool is the Sysmex® Inostics Liquid Biopsy (ONCOBEAM®) ctDNA Biomarker standard test (cf. sysmex-inostics.com; cdn2.hubspot.net/hubfs/5871980/OncoBEAM_ctDNA_Testing_in_Clinical_Practice_NSCLC_web.pdf. Further description and use of this assay can be found at Oxnard, G. R. et al. J. Clin. Oncol. 34 (28): 3375-3382 (2016); Wu, Y. L. et al. MA08.03 J. Thorac. Oncol. 12, S386 (2017); Mok, T. S. et al. N. Engl. J. Med. 376, 629-640 (2017); Thress K. et al. Poster presented at: European Society for Medical Oncology 2014 Congress; 2014 Sep. 26-30; Madrid, Spain; #1270P; and Murtaza M. et al. Nature. 497, 108-112 (2013)). This diagnostic test can detect any ESR1 mutation and their corresponding MAF with a lower level sensitivity limit of 0.05%.

The skilled artisan will recognize that different ESR1 mutations can result in ERα proteins with various mutations, including one or more of the following amino acid sequence mutations: E380Q, L536H, L536P, L536Q, L536R, Y537S, Y537C, Y537N, D538G or other mutations. In some embodiments, MAF for mutations in the ERα protein sequence at particular positions are evaluated in the methods disclosed herein, in particular mutations at amino acid positions 537 and/or 538 in SEQ ID NO: 1 (as opposed to ESR1 genetic mutations in the codons for those positions that have altered nucleic acid sequences but still encode wild type amino acid residues for the given positions within the ERα protein).

As used herein, a patient is said to have a "clonal" ERα mutation when the ctDNA diagnostic reveals that a particular ESR1 MAF (encoding a particular ERα mutation) value is greater than or equal to 0.5%, e.g., in a blood sample, but all other ESR1 MAF values (encoding any other ERα mutations) are less than 0.5%. So for example, a patient has a clonal Y537S ERα mutation if that patient's ctDNA encoding the Y537S mutation is found to have a MAF value greater than or equal to 0.5%, with all other ERα MAF values (including but not limited to D538G, L536H, L536P, L536Q, L536R, Y537C, Y537N, and E380Q MAF) values being, respectively, less than 0.5%. In another example, a patient has a clonal D538G ERα mutation if that patient's ctDNA encoding the D538G mutation is found to be greater than or equal to 0.5%, with all other ERα MAF values (including but not limited to Y537S, L536H, L536P, L536Q, L536R, Y537C, Y537N, and E380Q MAF) being, respectively, less than 0.5%.

In contrast, a patient is said to have a "polyclonal" ERα mutation when the ctDNA diagnostic reveals that two or more particular ERα MAF (encoding two or more particular ERα mutations) values are each greater than or equal to 0.5%. So for example, a patient has a polyclonal ERα mutation if that patient's ctDNA has MAFs encoding the Y537S mutation and the D538G mutation at greater than or equal to 0.5%.

In an embodiment of the invention, patients having a clonal Y537S ERα mutation may preferentially benefit from treatment with Compound 1 and pharmaceutically acceptable salts thereof. In another embodiment of the invention, patients having a clonal D538G ERα mutation may preferentially benefit from treatment with Compound 1 and pharmaceutically acceptable salts thereof.

Those of skill in the art will recognize that a patients' progesterone receptor (PgR) status may also be measured, e.g., in combination with a ERα MAF, to select patients most likely to respond to treatment with compound 1. PgR status may be detected by immunohistochemistry and/or by sequencing. In some embodiments of the disclosure, patients benefitting from treatment with Compound 1 are PgR positive in addition to having a clonal Y537S mutation or a clonal D538G mutation.

As used herein, "QTcF" is an electrocardiographic QT interval corrected for heart rate using the Fridericia's formula As used herein, "MTD" is the maximal tolerated dose.

As used herein, RP2D is the recommended phase 2 dose. It will be readily apparent to those skilled in the art that other suitable modifications and adaptations of the methods described herein may be made using suitable equivalents. Having now described the method in detail, the same will be more clearly understood by reference to the following examples, which are included for purposes of illustration only and are not intended to be limiting.

EXAMPLES

Example 1A—Summary

Compound 1 was tested in a first-in-human, Phase 1/2 study in women with locally advanced or metastatic ER+, HER2-negative breast cancer. In this multicenter study, women with locally advanced or metastatic ER+, HER2− breast cancer were treated with Compound 1 administered QD, PO over a 28-day cycle after progression on at least 1 hormonal therapy and at least 1 additional therapy/regimen.

The primary objective of the Phase 1 was to determine the MTD and RP2D in pretreated subjects with ER+, HER2− metastatic breast cancer. Secondary objectives included safety and antitumor activity. The primary objective of the Phase 2 was to estimate the efficacy of this agent in terms of objective response rate (ORR), clinical benefit rate (CBR), and progression-free survival (PFS). Secondary objectives included safety. The trial was designed to exclude a lower limit of ORR of 5% at one-sided level of significance of 0.05 and a power of 90%.

Example 1B—Demographics and Patient Characteristics

Over 30 months, 130 patients were enrolled; 47 in the Phase 1 part and 83 in the Phase 2 part of the trial. A total of 105 subjects, including 73 subjects on 450 mg were response-evaluable. As shown in Table 1, median age was 62 years (range: 31 to 87 years) and 82% had liver and/or lung metastases.

TABLE 1

Patient Demographics and Disease Characteristics

| Characteristics | N = 130 | (%) |
|---|---|---|
| Age: median (range); yrs | 62 | Range: (31-87) |
| Performance status | | |
| 0 | 61 | 47 |
| 1 | 69 | 53 |
| Measurable disease | 120 | 92 |
| Liver or lung metastases | 106 | 82 |
| Progesterone receptor (PgR) status | | |
| Positive | 51 | 39 |
| Negative | 50 | 38 |
| Unknown | 29 | 22 |
| PgR expression ≥10% | 38 | 29 |

The median number of prior therapies for metastatic disease was 3 (range: 1 to 10), with 41% of the patients receiving ≥4 prior therapies in the metastatic setting (Table 2). Prior CDK4/6 inhibitors, fulvestrant, and chemotherapy were received by 87%, 71%, and 54% of the patients, respectively. 75 patients (58%) have detectable ESR1 mutations using a plasma circulating DNA assay (Sysmex® Inostics Liquid Biopsy ONCOBEAM® ctDNA Biomarker standard test; limit of mutation detection: 0.05% mutant allele frequency).

TABLE 2

Prior Therapies for mBC

| Characteristics | N = 130 | (%) |
|---|---|---|
| Prior lines of therapy for mBC | | |
| Median (range) | 3 | Range: (1-10) |
| ≥4 prior lines | 53 | (41) |
| Prior therapy for mBC | | |
| Fulvestrant | 92 | (71) |
| CDK4/6i | 113 | (87) |
| Aromatase inhibitor (AI) | 107 | (82) |
| Chemotherapy | 70 | (54) |
| CDK4/6i + fulvestrant | 85 | (65) |
| CDK 4/6i + AI | 94 | (72) |
| Most recent therapy | | |
| Fulvestrant | 37 | (28) |
| CDK4/6i | 52 | (40) |
| AI | 33 | (25) |
| Chemotherapy | 38 | (29) |

Example 1C—Safety

The Phase 1 part evaluated once daily doses from 100 to 600 mg. No dose-limiting toxicities (DLTs) were observed at doses up to 450 mg and 2 DLTs were observed in 2 (Grade 3 fatigue and Grade 3 drug eruption) of 7 subjects on the 600 mg cohort. Consequently, the dose of 450 mg was selected as the RP2D.

Grade 2 or higher adverse events reported in ≥10% of subjects were anemia (20%), fatigue (16%), nausea (14%), diarrhea (11%) and AST increase (11%). Three cases of grade 4 AE were reported (serum bilirubin, urinary tract obstruction, and hyponatremia), all considered related to disease progression. Grade 1 sinus bradycardia (asymptomatic) was reported in 35% and Grade 2 (symptomatic, no intervention needed) was reported in 4%. Grade 2 and 3 QTcF prolongation were reported in 2 and 3 subjects, respectively. There were no treatment-related deaths.

Example 1D—Efficacy

In the response-evaluable group of subjects, 13 confirmed partial responses (PR, 12%. 90% confidence limits: 7.5%-19%), including 11 PRs (15%, 90% confidence limits: 8.7%-23.7) on 450 mg dose, were observed, thus achieving the primary objective of the trial (Table 3). Stable disease (SD) and clinical benefit rates (≥23 weeks) were 45% and 33% respectively at 450 mg and 46% and 34%, respectively on all doses. Responses were observed in heavily pretreated patients, patients with visceral metastases and in patients who received prior fulvestrant, prior CDK4/6 inhibitor, and/or prior chemotherapy, in the metastatic setting.

TABLE 3

Best Overall Response, Response Evaluable Set

| Best overall response | 450 mg N = 73 N (%) | All doses N = 105 N (%) |
|---|---|---|
| Complete response (CR) | 0 | 0 |
| Confirmed partial response (PR) | 11 (15) | 13 (12) |
| Stable disease (SD) | 33 (45) | 48 (46) |
| Progressive disease (PD) | 26 (36) | 37 (35) |
| Not evaluable | 3 (4) | 7 (7) |
| Clinical benefit rate[a] | 24 (33) | 36 (34) |

[a]Clinical benefit rate: CR + PR + SD lasting for ≥23 weeks

Using Kaplan-Meier analyses, among subjects who started at the 450 mg dose, median PFS was determined to be 3.8 months (95% CI:3.2-6.2).

Example 2—Discovery of the Effect of Clonal Y537S and Clonal D538G ESR1 Mutations Experiments conducted subsequent to those reported in Example 1 were directed to identify the parameters driving the activity of Compound 1 in the trial population. Two parameters were of particular interest: 1) PgR status, and 2) ESR1 mutant type and allele frequency. PFS was used in these analyses because it is a continuous variable. PgR positive status prior to treatment was expected to be associated with higher PFS in Compound 1-treated subjects because ER receptor is known to induce the expression of PgR (PgR+ indicates ER active and hence higher potential effect for an ER inhibitor). The effect of baseline circulating ESR1, of particular ESR1 mutants and their allele frequency was unknown.

The receiver operating characteristics (ROC) method was employed to search for potential biomarker/treatment interactions. When the effect of the detection of an ESR1 mutation in blood prior to treatment was investigated independently of the presence or absence of other ESR1 mutations, the Y537S ESR1 mutation appeared to predict an outcome of better than median PFS (3.8 months) with an area under the ROC curve of 0.857, p=0.007. The optimal criterion was a MAF of Y537S ESR1 in blood >0.34% with 100% sensitivity and 50% specificity to observe a PFS>3.8 months. A trend (AUC=738, p=0.13) was also observed when both the ESR1 mutations Y537S and/or D538G were taken together into account. No significant effect was observed with other mutations in the ROC analyses.

The effect of PgR positivity and the detection prior to treatment of ESR1 mutations Y537S and D538G on median PFS was then investigated using the Kaplan-Meier method. The effect of ESR1 clonality was also investigated since the presence of simultaneous clones of ESR1 mutations likely indicates very advanced or complex disease. Of note, the allele frequencies of the different ESR1 mutants were not identical, indicating the presence of multiple clones in a tumor, rather than multiple mutations in the same tumor ESR1 gene. For the purpose of these analyses, clonal Y537S was defined as ESR1 Y537S mutation detected in a pre-treatment whole blood sample at a mutant allele frequency (MAF)≥0.5% with a MAF for D538G<0.5%. Conversely, clonal D538G was defined as ESR1 D538G mutation detected in a pre-treatment whole blood sample at a MAF≥0.5% with a MAF for Y537S<0.5%.

In these analyses, among subjects who started at the 450 mg dose, median PFS was 3.8 months (95% CI:3.2-6.2) and 5.5 months in subjects with clonal ESR1 Y537S or clonal D538G mutations. When both PgR positivity and the presence or absence of clonal ESR1 Y537S or clonal D538G mutations were considered, PFS by subject subset was as shown in Table 4 and FIG. 5. The ROC method was used to create the criteria to sort the subjects as in Table 4 and FIG. 5. After trying each one of the ESR1 mutants, only when Y537S had a MAF value ≥0.5% (and the other mutants had a MAF value below 0.5%), or when D538G had a MAF value ≥0.5% (and the other mutants had a MAF below 0.5%), did the test predict a favorable outcome for the patient, according to ROC analysis. The highest clinical benefit was observed in subjects with tumors that were PgR+ and carried clonal ESR1 Y537S or clonal D538G mutations. The lowest median PFS was observed in subjects that carried concurrently both ESR1 Y537S and D538G mutations.

TABLE 4

Median Progression-Free-Survival (mPFS) by Subgroup Study 101

| | Subjects with PgR data started on 450 mg dose | | | |
|---|---|---|---|---|
| | PgR positive (defined as ≥1%) | | PgR negative | |
| Subgroup | mPFS (months) | N | mPFS (months) | N |
| Clonal Y537S | 13.0 | 6 | — | — |
| Clonal D538G | 4.5 | 10 | 1.7 | 3 |
| Clonal Y537S+ Clonal D538G (combined data) | 7.2 | 16 | 1.7 | 3 |
| Polyclonal | 2.6 | 3 | — | — |
| Y537S/D538G absent | 3.8 | 19 | 2.1 | 31 |
| All subjects | 5.5 | 38 | 2.1 | 34 |

PgR = progesterone receptor.

Figure 1:
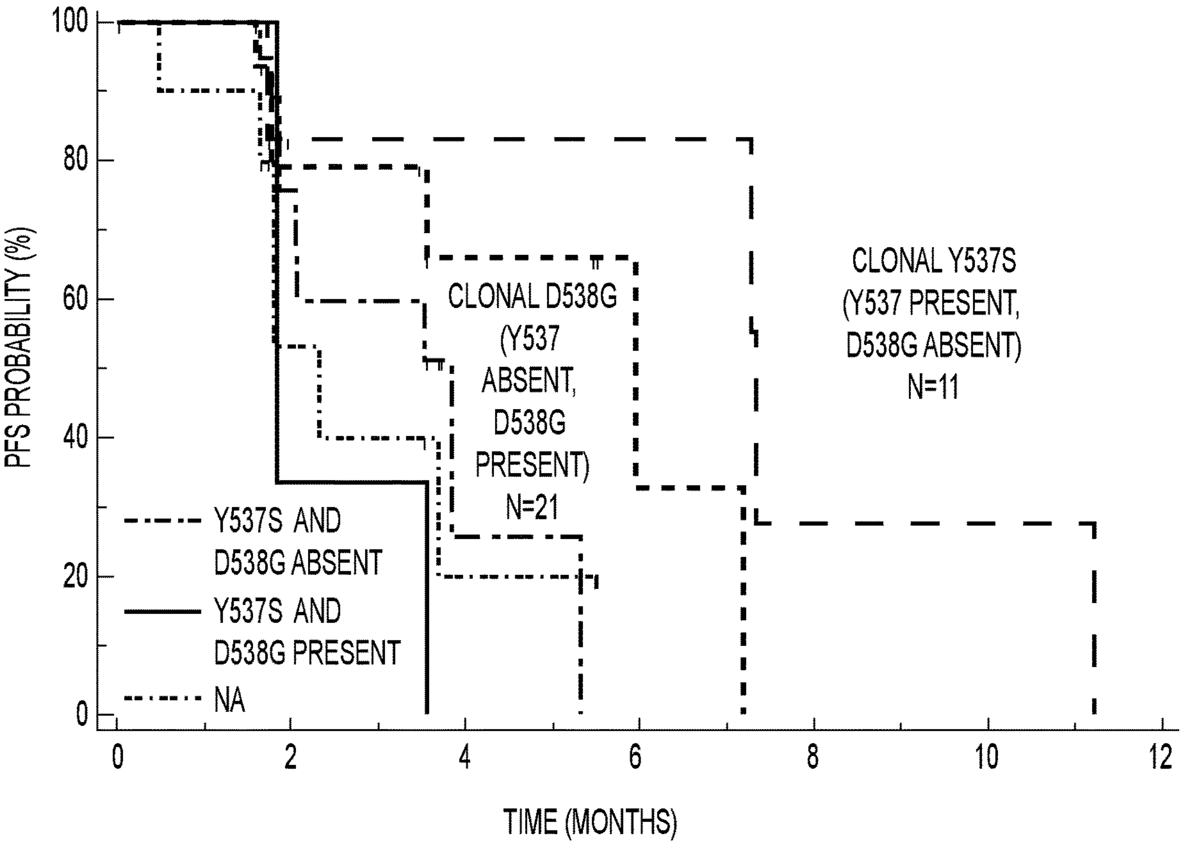
FIG. 1 shows that patients having clonal D538G or clonal Y537S ESR1 mutations have longer progression free survival (PFS) when treated with Compound 1, as discussed in Example 1 and Example 2.
Figure 2:
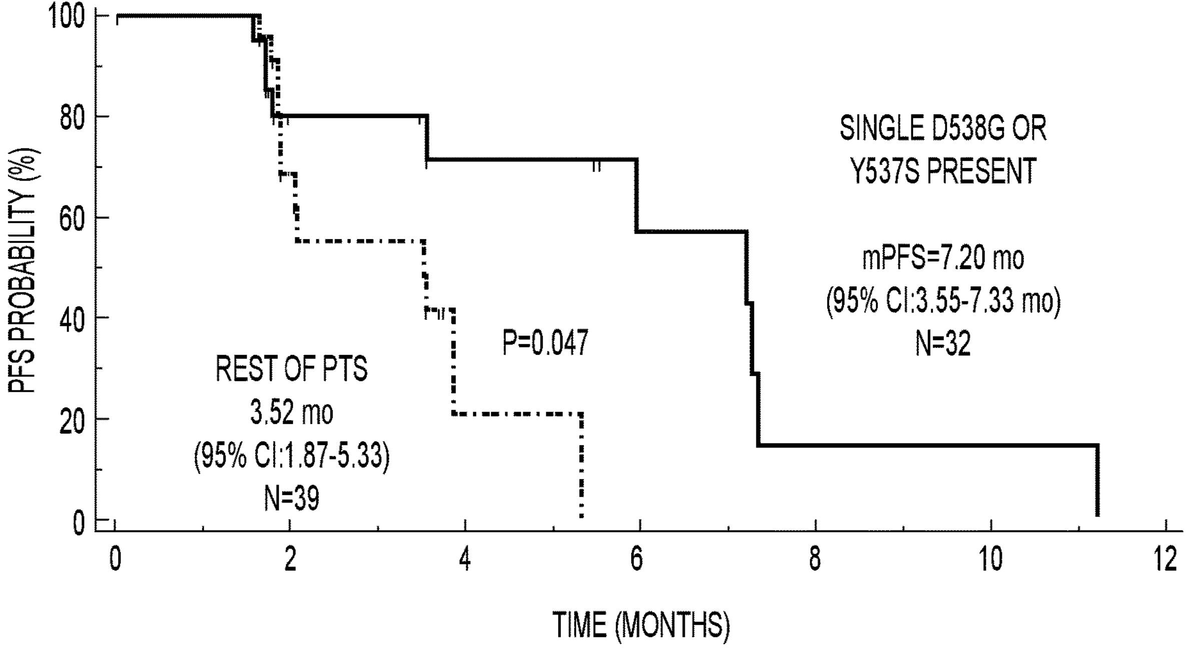
FIG. 2 shows combined PFS results for patients having clonal D538G and clonal Y537S ESR1 mutations compared to other patients.

FIG. 1 shows that clonal D538G or clonal Y537S ESR1 mutations are associated with Compound 1 activity, as discussed above. FIG. 2 shows the combined results for patients having clonal D538G or clonal Y537S ESR1 mutations. In both figures progression free survival probability is graphed as a percentage progression free versus time from randomization of the patient population. These results show a marked responsiveness in treatment outcome using Compound 1 in these groups of patients relative to patients treated with fulvestrant, which may be considered the standard of care. Fribbens, C. et al., J. Clin. Onc., 34(25): 2961-2968. These same mutations, whether clonal or polyclonal, are not positive prognosis factors for treatment with fulvestrant. Id.

Example 3A—Summary—Further Clinical Data Analysis

Following data analysis described above, patients remained in the Phase 2 study reported in Example 1, and clinical data collection continued. The primary objective of this study was to estimate the efficacy of Compound 1 in terms of best overall response rate (ORR), duration of response (DoR), clinical benefit rate, and progression-free survival (PFS) in all subjects and in those with and without ERα mutation (ERαMUT).

Example 3B—Demographics and Patient Characteristics 83 patients were treated with 450 mg in the Phase 2 study of Example 1. Additionally, 11 patients who were treated with 450 mg in the Phase 1 part of the trial (also discussed in Example 1) have been grouped with these 83 Phase 2 patients for discussion in this example. That resulted in a total of 94 patients who were treated with 450 mg. Patients were heavily pretreated, and 85% of the patients received prior CDK4/6 inhibitors.

TABLE 5

Patient Demographics and Disease Characteristics (Example 3)

| Characteristics | N = 94, (%)/Range |
|---|---|
| Age: median (range); years | 62 (38-87) |
| Prior lines of therapy for mBC[1] | |
| Median (range) | 3 (1-8) |
| ≥4 prior lines | 33 (35) |
| Prior therapy for mBC | |
| CDK4/6 inhibitor | 80 (85) |
| + Fulvestrant | 62 (66) |
| + Aromatase inhibitor | 63 (67) |
| Aromatase inhibitor | 75 (80) |
| Fulvestrant | 68 (72) |
| Chemotherapy | 47 (50) |
| ECOG OS | |
| 0 | 47 (50) |
| 1 | 47 (50) |
| Liver or lung metastases | 76 (81) |
| Bone only (no measurable disease) | 9 (10) |
| ESR1 subtype | |
| Clonal Y537S or Clonal D538G | 29 (31) |
| Clonal Y537S[2] | 10 (11) |

TABLE 5-continued

Patient Demographics and Disease Characteristics (Example 3)

| Characteristics | N = 94, (%)/Range |
|---|---|
| Clonal D538G[3] | 19 (20) |
| Polyclonal Y537S and D538G | 4 (4) |
| Y537S and D538G negatives | 61 (65) |

[1]mBC includes metastatic or locally advanced disease
[2]Y537S at MAF ≥0.5%, D538G MAF <0.5%
[3]D538G at MAF ≥0.5%, Y537S MAF <0.5%
ECOG PS: Eastern Cooperative Oncology Group performance status
MAF: Mutant Allele Frequency

Example 3C—Efficacy

Responses were observed in heavily pretreated patients, patients with visceral metastases, and patients who received prior fulvestrant, prior CDK4/6 inhibitor, and/or prior chemotherapy, in the metastatic setting (see Table 6).

TABLE 6

Best Overall Response in the Response-Evaluable Set[1]

| Response | Response 450 mg, N = 72 n (%) |
|---|---|
| Complete response | 0 |
| Confirmed partial response | 12 (17) |
| Stable disease | 31 (43) |
| Progressive disease | 27 (38) |
| Not evaluable | 2 (3) |
| ORR (%) (95% confidence interval)[2] | 17 (9, 27) |
| Median duration of response (mo) (min, max) | 7.5 (3.5, 16.6) |
| Median time to response (mo) (min, max) | 2.7 (1.6, 5.5) |
| Clinical benefit rate (CR + PR + SD ≥ 23 weeks) | 29 (40) |

[1]Response-Evaluable Set includes subjects who received at least one dose of study drug and have measurable disease at baseline and at least one post-baseline adequate evaluation
[2]Median duration of response is not reached using Kaplan-Meier estimation, and descriptive median is reported
CR: complete response
ORR: objective response
PR: partial response
SD: stable disease Three partial responses (30%) and four stable disease (40%) were observed in 10 patients in whom clonal ESR1 Y537S was the main ERα driver (see Table 7).

Median progression free survival in all 94 patients and in the 10 patients with clonal ESR1 Y537S was 5.1 months and 7.3 months, respectively.

Figure 3:
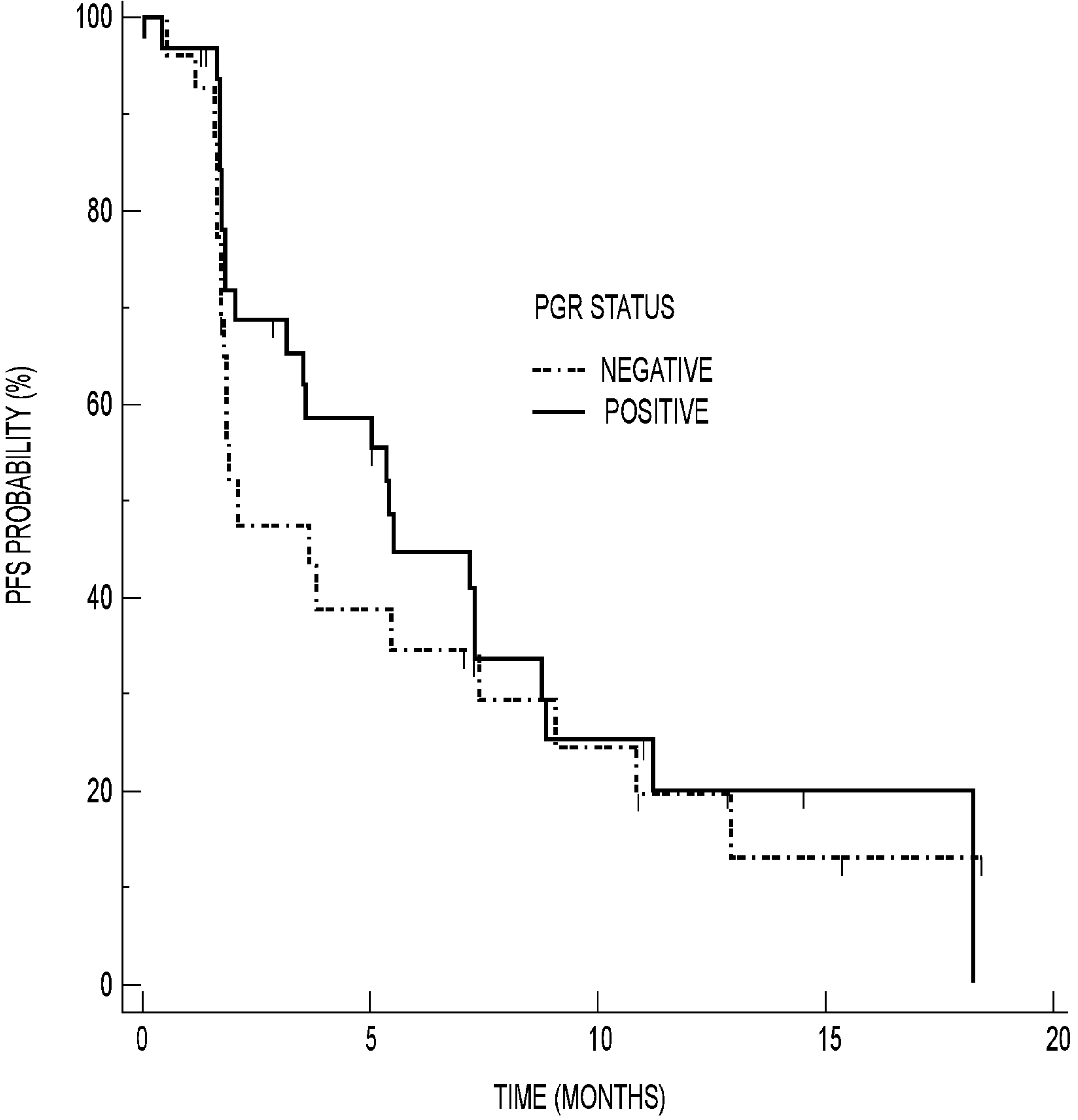
FIG. 3 shows potential higher efficacy in patients with PgR+ tumors as reported in Example 3. The text in the inset reads as follows.

Potential higher activity was observed in patients with Progesterone Receptor Positive (PgR+) and in those with ESR1 Y537S (see FIG. 3 and FIG. 4 and Table 7).

TABLE 7

Best Overall Response by ESRI Subtype in Response-Evaluable Set[1]

| | Clonal Y537S (N = 10) n (%) | Clonal D538G (N = 17) n (%) | Clonal Y537S Or Clonal D538G (N = 27) n (%) | Polyclonal Y537S and D538G (N = 2) n (%) | Y537S and D538G Negatives (N = 43) n (%) |
|---|---|---|---|---|---|
| Complete response | 0 | 0 | 0 | 0 | 0 |
| Confirmed partial response | 3 (30) | 0 | 3 (11) | 0 | 9 (21) |
| Stable disease | 4 (40) | 10 (59) | 14 (52) | 1 (50) | 16 (37) |
| Progressive disease | 3 (30) | 7 (41) | 10 (37) | 1 (50) | 16 (37) |

TABLE 7-continued

Best Overall Response by ESRI Subtype in Response-Evaluable Set[1]

| | Clonal Y537S (N = 10) n (%) | Clonal D538G (N = 17) n (%) | Clonal Y537S Or Clonal D538G (N = 27) n (%) | Polyclonal Y537S and D538G (N = 2) n (%) | Y537S and D538G Negatives (N = 43) n (%) |
|---|---|---|---|---|---|
| Not evaluable | 0 | 0 | 0 | 0 | 2 (5) |
| Clinical benefit rate | 6 (60) | 6 (35) | 12 (44) | 1 (50) | 16 (37) |
| Median PFS (mo) | 7.3 | 5.4 | 5.4 | 3.5 | 3.8 |

[1]Response-Evaluable Set includes subjects who received at least one dose of study drug and have measurable disease at baseline and at least one post-baseline adequate evaluation
[2]Median PFS is calculated for the full analysis set, including subjects who received at least one dose of study drug
PFS, progression-free survival Example 3D—Conclusions Based on the results of the data analysis in Example 3, we concluded that Compound 1 monotherapy (that is, Compound 1 monotherapy), at once a daily dose of 450 mg demonstrated anti-tumor activity in heavily pretreated ER+, HER2−, metastatic breast cancer patients. Confirmed responses were observed in patients with visceral disease, ESR1 mutations, and after prior therapy with fulvestrant, CDK4/6 inhibitors, and chemotherapy. Data suggested a potential higher activity of Compound 1 in patients with ESR1 Y537S clonal mutations and in patients with PgR+ tumors.

Selected sequences:
ER Amino Acid Sequence (SEQ ID NO: 1)

MTMTLHTKASGMALLHQIQGNELEPLNRPQLKIPLERPLGEVYLDSSKPAVYNYPEGAA

YEFNAAAAANAQVYGQTGLPYGPGSEAAAFGSNGLGGFPPLNSVSPSPLMLLHPPPQLS

PFLQPHGQQVPYYLENEPSGYTVREAGPPAFYRPNSDNRRQGGRERLASTNDKGSMAM

ESAKETRYCAVCNDYASGYHYGVWSCEGCKAFFKRSIQGHNDYMCPATNQCTIDKNR

RKSCQACRLRKCYEVGMMKGGIRKDRRGGRMLKHKRQRDDGEGRGEVGSAGDMRA

ANLWPSPLMIKRSKKNSLALSLTADQMVSALLDAEPPILYSEYDPTRPFSEASMMGLLT

NLADRELVHMINWAKRVPGFVDLTLHDQVHLLECAWLEILMIGLVWRSMEHPGKLLF

APNLLLDRNQGKCVEGMVEIFDMLLATSSRFRMMNLQGEEFVCLKSIILLNSGVYTFLSS

TLKSLEEKDHIHRVLDKITDTLIHLMAKAGLTLQQQHQRLAQLLLILSHIRHMSNKGME

HLYSMKCKNVVPLYDLLLEMLDAHRLHAPTSRGGASVEETDQSHLATAGSTSSHSLQK

YYITGEAEGFPATV

Wild Type sequence for ESR1

(SEQ ID NO: 2)

GTCGCCTCTAACCTCGGGCTGTGCTCTTTTTCCAGGTGGCCCGCCGGTTTCTGAGCCT

TCTGCCCTGCGGGGACACGGTCTGCACCCTGCCCGCGGCCACGGACCATGACCATG

ACCCTCCACACCAAAGCATCTGGGATGGCCCTACTGCATCAGATCCAAGGGAACGA

GCTGGAGCCCCTGAACCGTCCGCAGCTCAAGATCCCCCTGGAGCGGCCCCTGGGCG

AGGTGTACCTGGACAGCAGCAAGCCCGCCGTGTACAACTACCCCGAGGGCGCCGCC

TACGAGTTCAACGCCGCGGCCGCCGCCAACGCGCAGGTCTACGGTCAGACCGGCCT

CCCCTACGGCCCCGGGTCTGAGGCTGCGGCGTTCGGCTCCAACGGCCTGGGGGGTTT

CCCCCCACTCAACAGCGTGTCTCCGAGCCCGCTGATGCTACTGCACCCGCCGCCGCA

GCTGTCGCCTTTCCTGCAGCCCCACGGCCAGCAGGTGCCCTACTACCTGGAGAACGA

GCCCAGCGGCTACACGGTGCGCGAGGCCGGCCCGCCGGCATTCTACAGGCCAAATT

CAGATAATCGACGCCAGGGTGGCAGAGAAAGATTGGCCAGTACCAATGACAAGGG

AAGTATGGCTATGGAATCTGCCAAGGAGACTCGCTACTGTGCAGTGTGCAATGACTA

TGCTTCAGGCTACCATTATGGAGTCTGGTCCTGTGAGGGCTGCAAGGCCTTCTTCAA

GAGAAGTATTCAAGGACATAACGACTATATGTGTCCAGCCACCAACCAGTGCACCA

TTGATAAAAACAGGAGGAAGAGCTGCCAGGCCTGCCGGCTCCGCAAATGCTACGAA

GTGGGAATGATGAAAGGTGGGATACGAAAAGACCGAAGAGGAGGGAGAATGTTGA

-continued

AACACAAGCGCCAGAGAGATGATGGGGAGGGCAGGGGTGAAGTGGGGTCTGCTGG

AGACATGAGAGCTGCCAACCTTTGGCCAAGCCCGCTCATGATCAAACGCTCTAAGA

AGAACAGCCTGGCCTTGTCCCTGACGGCCGACCAGATGGTCAGTGCCTTGTTGGATG

CTGAGCCCCCCATACTCTATTCCGAGTATGATCCTACCAGACCCTTCAGTGAAGCTT

CGATGATGGGCTTACTGACCAACCTGGCAGACAGGGAGCTGGTTCACATGATCAAC

TGGGCGAAGAGGGTGCCAGGCTTTGTGGATTTGACCCTCCATGATCAGGTCCACCTT

CTAGAATGTGCCTGGCTAGAGATCCTGATGATTGGTCTCGTCTGGCGCTCCATGGAG

CACCCAGGGAAGCTACTGTTTGCTCCTAACTTGCTCTTGGACAGGAACCAGGGAAAA

TGTGTAGAGGGCATGGTGGAGATCTTCGACATGCTGCTGGCTACATCATCTCGGTTC

CGCATGATGAATCTGCAGGGAGAGGAGTTTGTGTGCCTCAAATCTATTATTTTGCTT

AATTCTGGAGTGTACACATTTCTGTCCAGCACCCTGAAGTCTCTGGAAGAGAAGGAC

CATATCCACCGAGTCCTGGACAAGATCACAGACACTTTGATCCACCTGATGGCCAAG

GCAGGCCTGACCCTGCAGCAGCAGCACCAGCGGCTGGCCCAGCTCCTCCTCATCCTC

TCCCACATCAGGCACATGAGTAACAAAGGCATGGAGCATCTGTACAGCATGAAGTG

CAAGAACGTGGTGCCCCTCTATGACCTGCTGCTGGAGATGCTGGACGCCCACCGCCT

ACATGCGCCCACTAGCCGTGGAGGGGCATCCGTGGAGGAGACGGACCAAAGCCACT

TGGCCACTGCGGGCTCTACTTCATCGCATTCCTTGCAAAAGTATTACATCACGGGGG

AGGCAGAGGGTTTCCCTGCCACGGTCTGAGAGCTCCCTGGCTCCCACACGGTTCAGA

TAATCCCTGCTGCATTTTACCCTCATCATGCACCACTTTAGCCAAATTCTGTCTCCTG

CATACACTCCGGCATGCATCCAACACCAATGGCTTTCTAGATGAGTGGCCATTCATT

TGCTTGCTCAGTTCTTAGTGGCACATCTTCTGTCTTCTGTTGGGAACAGCCAAAGGG

ATTCCAAGGCTAAATCTTTGTAACAGCTCTCTTTCCCCCTTGCTATGTTACTAAGCGT

GAGGATTCCCGTAGCTCTTCACAGCTGAACTCAGTCTATGGGTTGGGGCTCAGATAA

CTCTGTGCATTTAAGCTACTTGTAGAGACCCAGGCCTGGAGAGTAGACATTTTGCCT

CTGATAAGCACTTTTTAAATGGCTCTAAGAATAAGCCACAGCAAAGAATTTAAAGTG

GCTCCTTTAATTGGTGACTTGGAGAAAGCTAGGTCAAGGGTTTATTATAGCACCCTC

TTGTATTCCTATGGCAATGCATCCTTTTATGAAAGTGGTACACCTTAAAGCTTTTATA

TGACTGTAGCAGAGTATCTGGTGATTGTCAATTCATTCCCCCTATAGGAATACAAGG

GGCACACAGGGAAGGCAGATCCCCTAGTTGGCAAGACTATTTTAACTTGATACACTG

CAGATTCAGATGTGCTGAAAGCTCTGCCTCTGGCTTTCCGGTCATGGGTTCCAGTTA

ATTCATGCCTCCCATGGACCTATGGAGAGCAGCAAGTTGATCTTAGTTAAGTCTCCC

TATATGAGGGATAAGTTCCTGATTTTTGTTTTTATTTTTGTGTTACAAAAGAAAGCCC

TCCCTCCCTGAACTTGCAGTAAGGTCAGCTTCAGGACCTGTTCCAGTGGGCACTGTA

CTTGGATCTTCCCGGCGTGTGTGTGCCTTACACAGGGGTGAACTGTTCACTGTGGTG

ATGCATGATGAGGGTAAATGGTAGTTGAAAGGAGCAGGGGCC

---

I claim:

1. A method of treating breast cancer comprising administering (Compound 1)

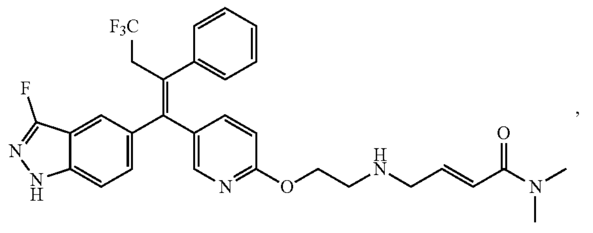

, or a pharmaceutically acceptable salt thereof, to a patient, wherein the method comprises determining a first mutant allele frequency ("MAF") value of a first ERα mutant and a second MAF value of a second ERα mutant in the patient, and administering to the patient a therapeutically effective amount of Compound 1 or a pharmaceutically acceptable salt thereof if the first MAF value is greater than or equal to 0.5% and the second MAF value is less than 0.5%, wherein said first ERα mutant is Y537S or D538G.

2. The method of claim 1, wherein said first ERα mutant is Y537S.

3. The method of claim 2, wherein said second ERα mutant is D538G.

4. The method of claim 2, wherein said second ERα mutant is L536H, L536P, L536Q, L536R, Y537C, Y537N, or E380Q.

5. The method of claim 1, wherein said first ERα mutant is D538G.

6. The method of claim 5, wherein said second ERα mutant is Y537S.

7. The method of claim 5, wherein said second ERα mutant is L536H, L536P, L536Q, L536R, Y537C, Y537N, or E380Q.

8. The method of claim 2, wherein said first MAF value is greater than 1.0%.

9. The method of claim 5, wherein said first MAF value is greater than 1.0%.

10. The method of claim 3, wherein said second MAF value is less than 0.1%.

11. The method of claim 6, wherein said second MAF value is less than 0.1%.

12. The method of claim 1, wherein said patient has PgR positive status.

13. The method of claim 1, wherein the first MAF value and the second MAF value are measured in a blood sample from the patient.

14. The method of claim 1, wherein the first MAF value and the second MAF value are measured in cfDNA from a blood sample from the patient.

15. The method of claim 1, wherein the breast cancer is a metastatic breast cancer.

16. The method of claim 1, wherein the breast cancer is an HER2-negative breast cancer.

17. The method of claim 1, wherein said patient has been treated with at least one therapy selected from the group consisting of fulvestrant, a CDK 4/6 inhibitor, and chemotherapy prior to the administering of Compound 1 or a pharmaceutically acceptable salt thereof to said patient.

* * * * *